United States Patent [19]
Weissman et al.

[11] Patent Number: 5,564,629
[45] Date of Patent: Oct. 15, 1996

[54] ORAL IRRIGATING APPARATUS AND METHOD FOR SELECTIVELY MIXING AND DISCHARGING A PLURALITY OF LIQUIDS

[75] Inventors: William R. Weissman, 4418 Vineland Ave., North Hollywood, Calif. 91602; Peter Liapis, Los Angeles, Calif.; George Sanchez; Bernardo Baran, both of Woodlands Hill, Calif.

[73] Assignee: William R. Weissman, North Hollywood, Calif.

[21] Appl. No.: 255,702

[22] Filed: Jun. 7, 1994

[51] Int. Cl.6 ............................................. B05B 7/28
[52] U.S. Cl. ..................... 239/8; 239/310; 239/313; 239/317; 239/322; 601/165; 604/83
[58] Field of Search ........................... 239/310, 313, 239/317, 322, 8; 601/165, 162; 604/82–85

[56] References Cited

U.S. PATENT DOCUMENTS

| | | | |
|---|---|---|---|
| 2,323,618 | 7/1943 | Ottoson | 239/322 |
| 2,867,230 | 1/1959 | Bletcher et al. | |
| 3,225,759 | 12/1965 | Drapen et al. | 601/165 |
| 3,500,824 | 3/1970 | Gilbert | 601/165 |
| 3,780,910 | 12/1973 | Wagner | 239/313 |
| 3,820,532 | 6/1974 | Eberhardt et al. | 601/165 |
| 4,043,337 | 8/1977 | Baugher. | |
| 4,265,229 | 5/1981 | Rice et al. | 601/165 |
| 4,564,005 | 1/1986 | Merchand et al. | 601/165 |
| 4,793,331 | 12/1988 | Stewart | 601/165 |
| 5,004,158 | 4/1991 | Halem et al. | 239/313 |
| 5,218,956 | 6/1993 | Handler et al. | 601/165 |
| 5,220,914 | 6/1993 | Thompson | 601/165 |

Primary Examiner—Andres Kashnikow
Attorney, Agent, or Firm—Ashen, Golant & Lippman

[57] ABSTRACT

An apparatus (20, 30) operative from a first liquid pressure only and configured to generate and selectively direct a stream of first liquid or a third liquid is disclosed. Since no electrical power is used, the apparatus can be safely operated in any moist environments (e.g. a shower). In preferred embodiments, the apparatus is configured to operate in series with a showerhead (22) and a sink tap (32) for dental irrigation. Either water or dental solution which is comprised of water mixed with dental concentrate, can be independently selected. A mixer valve (48) controls the concentration of the irrigating solution. A handheld syringe (40) contains all other controls necessary for operation.

23 Claims, 7 Drawing Sheets

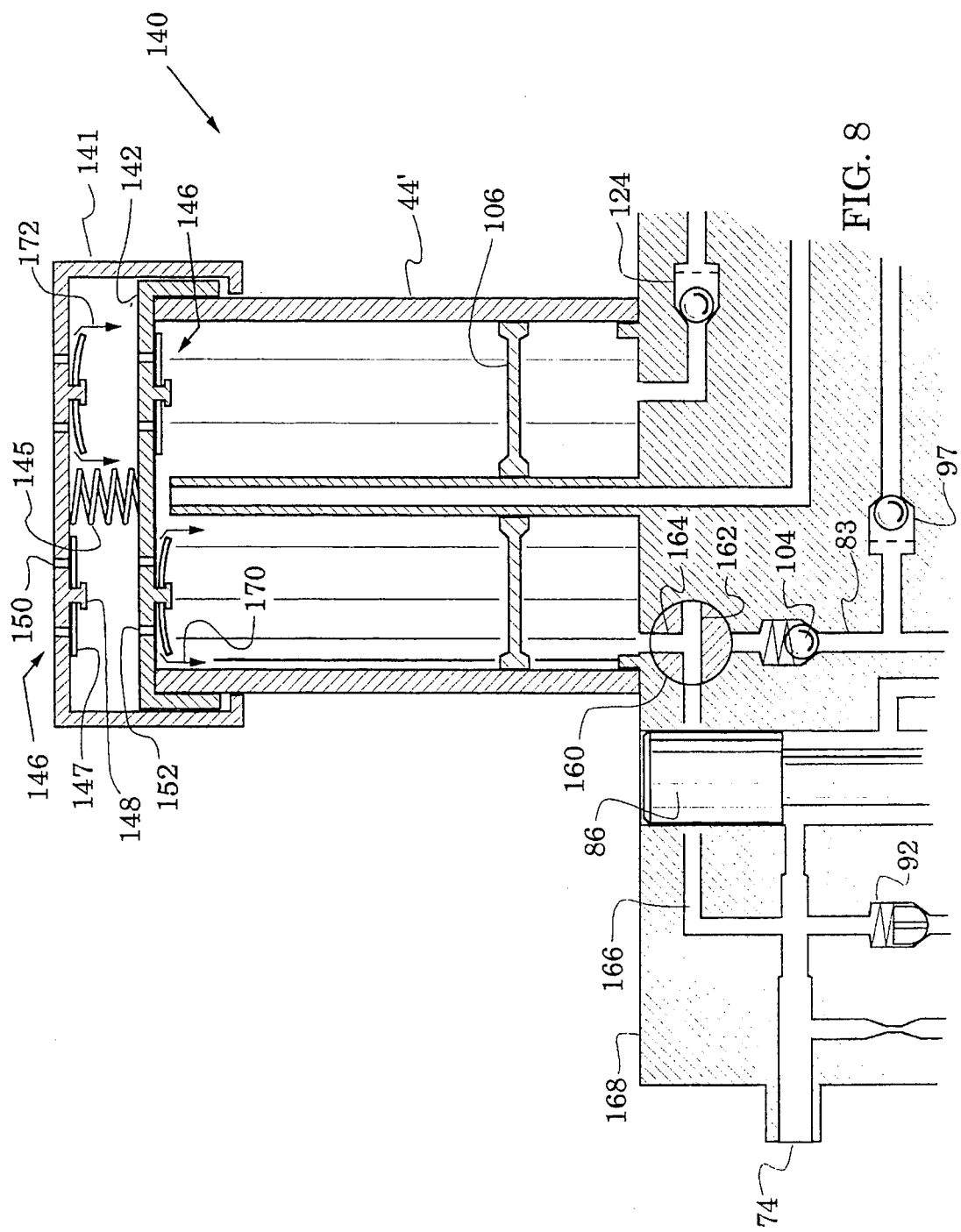

5,564,629

ORAL IRRIGATING APPARATUS AND METHOD FOR SELECTIVELY MIXING AND DISCHARGING A PLURALITY OF LIQUIDS

TECHNICAL FIELD

The present invention relates generally to a dental liquid mixing apparatus and more particularly to such apparatus for mixing and applying a cleansing stream to teeth and/or gums.

BACKGROUND ART

Dental oral irrigating apparatus presently exist for generating and applying a stream of liquid to areas of a person's mouth. Some such apparatus are electrically powered and present potential danger to the user. Other such apparatus are powered and controlled by the liquid pressure from a water line. Examples of such latter units are disclosed in prior U.S. patents Nos. to Handler, et al., 5,218,956, to Gilbert, 3,500,824, to Drapen, et al., 3,225,759, to Chernack, 4,979,503. Such prior apparatus allow the user to selectively provide a discharge of only water or of water combined with a second liquid such as medication, mouthwash or the like. The apparatus disclosed by the above-noted patents all provide a reservoir for the secondary liquid mounted on the hand-holdable control and dispensing unit, which adds substantially to the size and weight of that unit. Further, because of the limited amount of secondary liquid that can be held in such a reservoir, the reservoir would have to be refilled frequently. These prior art apparatus also have various other limitations and deficiencies. Gilbert has no way to adjust the ratio of mix of the two liquids. In Handler the control of the flows of the primary and the additive liquids is controlled by two separately independently operable control levers so that the desired proportioning between the two liquids has to be reestablished each time the device is turned back on. In Drapen there are two separate controls on the handheld unit, one a depressible off/on switch, the other a rotatable element for controlling flow of the second liquid and which would appear to require the second hand of the user to operate. In Chernack there are two separate flow controls on the handheld unit. One an on/off for the second liquid and the other a water input flow control, with the amount or mixture of the second liquid being fixed with relation to the water flow.

Other water-powered oral irrigating devices disclosed secondary liquid reservoirs on the base, but lacked user control over the mixing ratio: See Harlem, et al., U.S. Pat. No. 5,004,158 and Thompson,

DISCLOSURE OF INVENTION

The present invention involves a liquid 1 pressure powered oral irrigating apparatus which enables a method of mixing apparatus a first liquid with a second liquid concentrate to create an irrigating stream third liquid and dispenses a selectable one of the first and second.

Apparatus in accordance with the invention are characterized by a container with a dispenser piston arranged therein coupled to a mixing structure to dispense a third liquid in response to pressurized first liquid received on a first side of the dispenser piston. The apparatus is further characterized by a control valve configured to selectively connect a pressurized first liquid supply to the dispenser piston first side and to selectively route either the first liquid or the third liquid to an orifice defined by the control valve.

In a preferred embodiment the irrigating solution (third liquid) is formed by mixing pressurized first liquid adjoining the dispenser piston first side and a second liquid disposed between the piston second side and the container.

In a preferred embodiment a diverter valve is configured to divert first liquid from the pressurized liquid supply to a tap port in response to first liquid received from the control valve when it connects the liquid 1 supply to first and second control ports defined by the control valve. Thus a liquid tap such as a showerhead or sinktap can be selectively used with the apparatus.

In accordance with a feature of the invention, the apparatus is entirely powered by first liquid pressure enabling it to be Safely used in moist environments (e.g. home showers).

In accordance with another feature of the invention a mixer valve selectively restricts passages communicating with the dispenser first and second sides to adjust the concentration of the third liquid.

The novel features of the invention are set forth With particularity in the appended claims. The invention will be best understood from the following description when read in conjunction with the accompanying drawings.

BRIEF DESCRIPTION OF DRAWINGS

FIG. 8 is an inverted, enlarged view of a portion of FIG. 3 illustrating another preferred operational embodiment.

MODES FOR CARRYING OUT THE INVENTION

Figure 1:
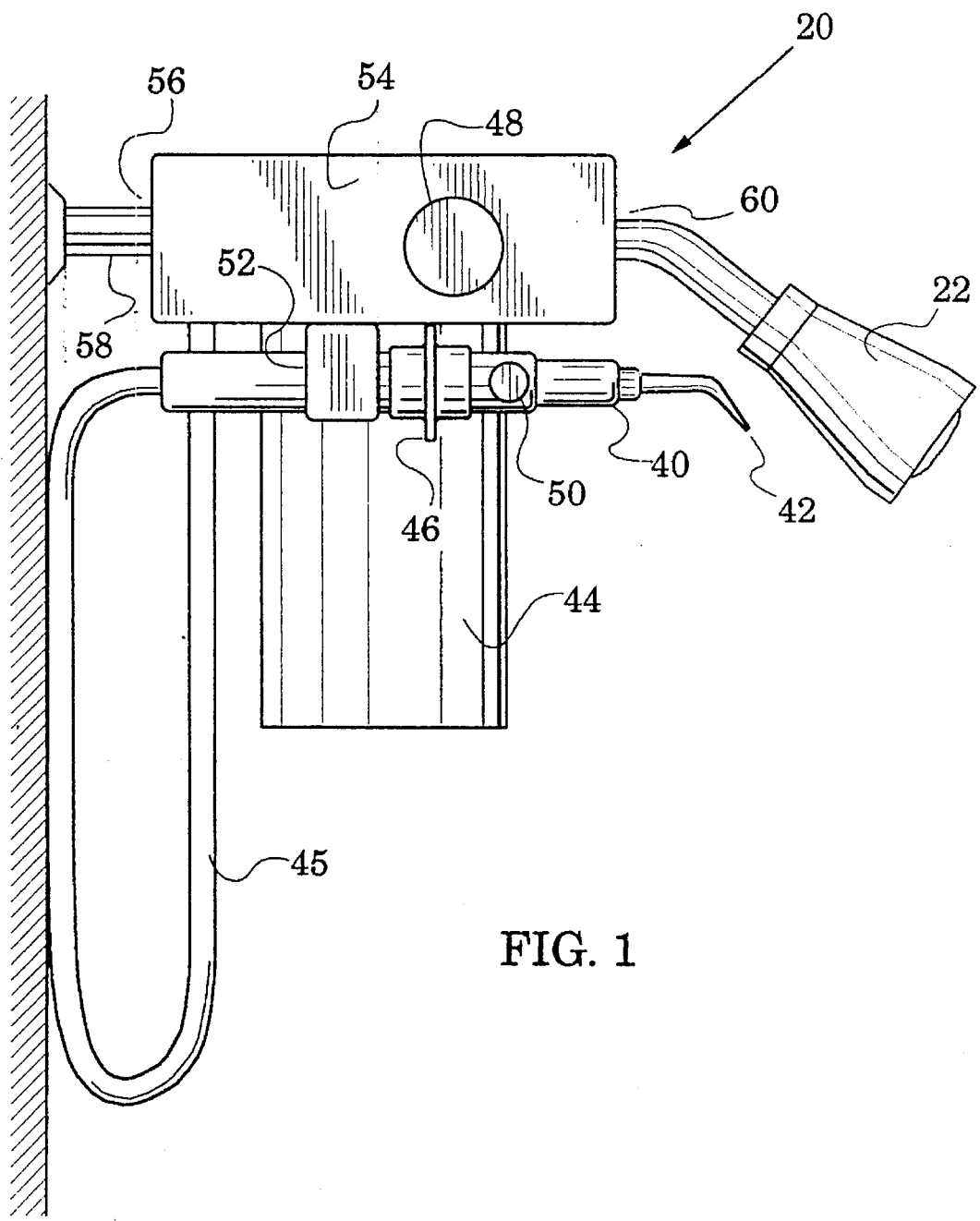
FIG. 1 is an elevation view of a preferred apparatus embodiment operative from a pressurized first liquid supply, in accordance with the present invention, installed in series with a shower head.
Figure 2:
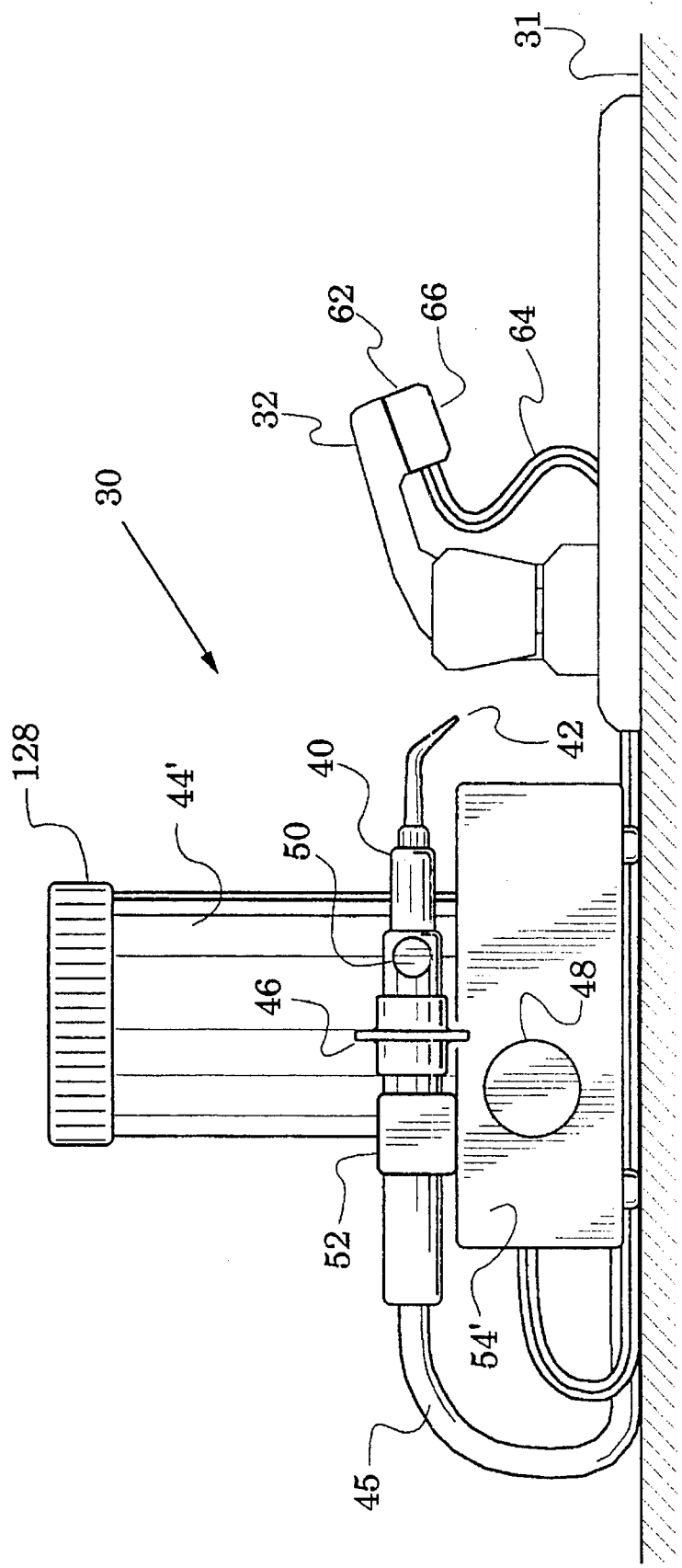
FIG. 2 is an elevation view of another preferred apparatus embodiment installed in series with a sink tap.

FIG. 1 is an elevation view of a preferred embodiment 20 in accordance with the present invention, installed in series with a shower head 22 and FIG. 2 is an elevation view of another preferred embodiment 30 placed on a countertop 31 and installed in series with a sink tap 32.

These figures illustrate embodiments of the invention configured for a specific application, i.e. irrigation of the spaces between the teeth and gums in a home environment.

Apparatus in accordance with the invention may be configured to mix a first liquid with a second liquid to form a third liquid and to eject a liquid stream selected to be either the first liquid or the third liquid. Water is an exemplary first liquid while examples of second liquid include liquid medicaments and mouthwashes. Thus, it should be understood that the following description of the embodiments 20, 30 is exemplary of the variety of configurations, and uses thereof, in which the invention may be realized.

The embodiments 20, 30 each have a handheld syringe 40 defining an orifice 42 and respective containers 44, 44' which may be filled with one of various dental concentrates (e.g. mouthwash). The syringe 40 is located at the end of a connecting hose 45 and configured to be held in one hand for manipulation therewith to direct a stream of first liquid or third from the orifice 42 against the teeth and gums for cleaning thereof.

A sliding sleeve 46 on the syringe 40 may be operated with thumb and fingers to select between an "off" and two "on" positions; one in which only water is directed from the orifice 42 and a second in which a mixture of water and dental concentrate (to yield third liquid) is directed from the orifice : 42. The mixture proportions are controlled with a mixture knob 48 while the flow rate of the stream may be adjusted with a flow rate knob 50.

In each of the embodiments 20, 30 the syringe 40 may, when not in use, be placed in a holder 52 attached to respective bases 54, 54'. In the embodiment 20, the base 54 defines an input port 56 which screws onto the wall pipe 58 and an output port 60 which receives the shower head 22. In the embodiment 30, a diverter head 62 is attached to the sink tap 32 to send water through a double hose 64 to the base 54' and back to issue through the diverter output 66.

In accordance with a feature of the invention, the apparatus is operative from a pressurized water supply. It is powered only by water pressure and no electricity, therefore there is no danger to a user, especially around plumbing electrical grounds. This even allows use of the apparatus in a shower as shown in FIG. 1.

The syringe 40 is conveniently located close to the tap or showerhead and can be operated with only the hand holding it except for adjusting the mixture knob 48 on an infrequent basis, and the user does not have to reach for any other controls (e.g. an on/off electrical switch).

In accordance with other features of the invention, water or a mixture of water and dental concentrate may be selected and the dental concentrate placed in the container 44 (44') may be controllably diluted by adjusting the mixture knob 48. This allows the use, in the container 44, 44', of a stronger concentrate so that the replacement period of the concentrate is extended.

Figure 3:
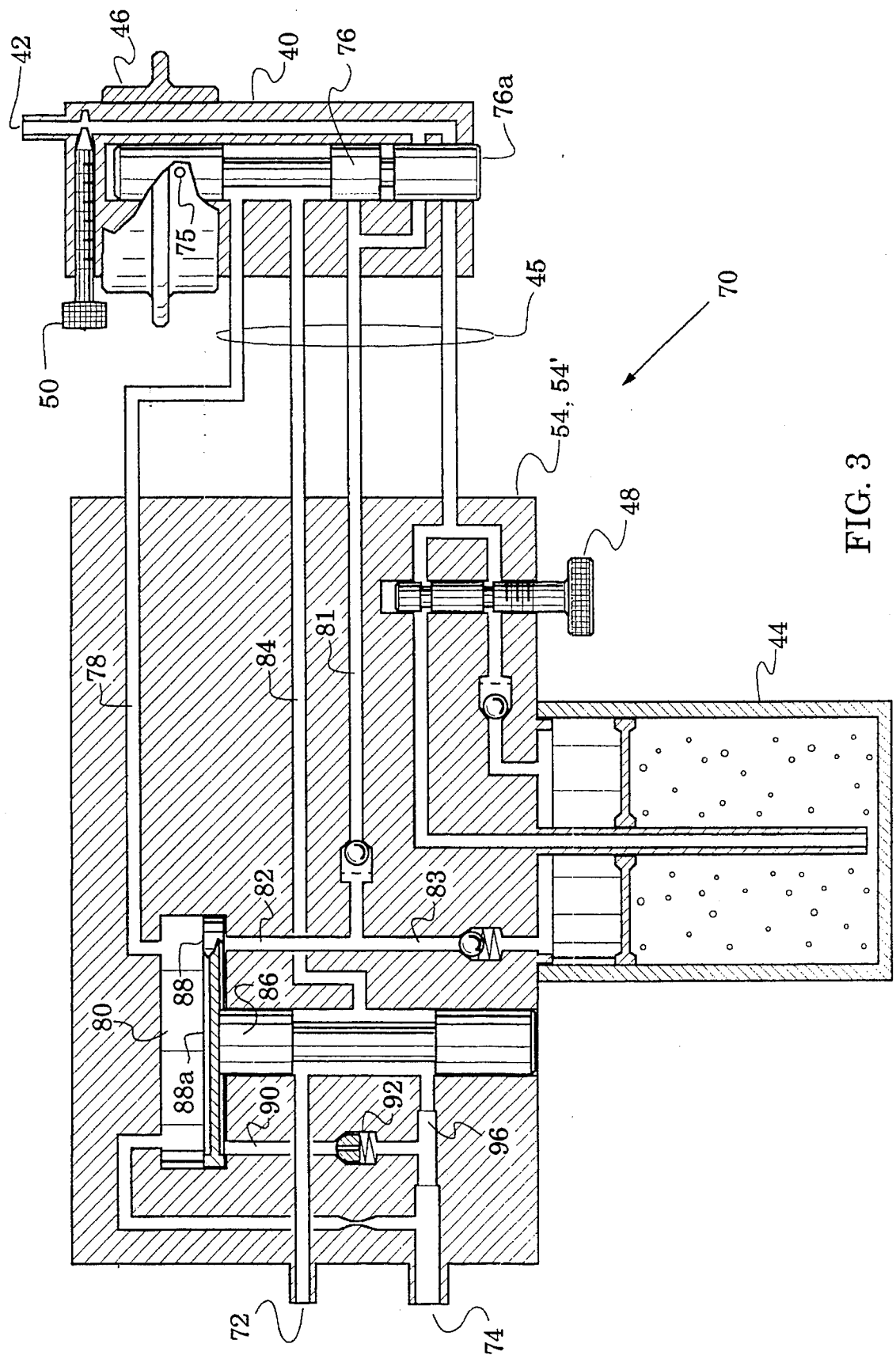
FIG. 3 is a schematic illustrating a preferred operational embodiment of the apparatus of FIGS. 1 and 2.
Figure 4:
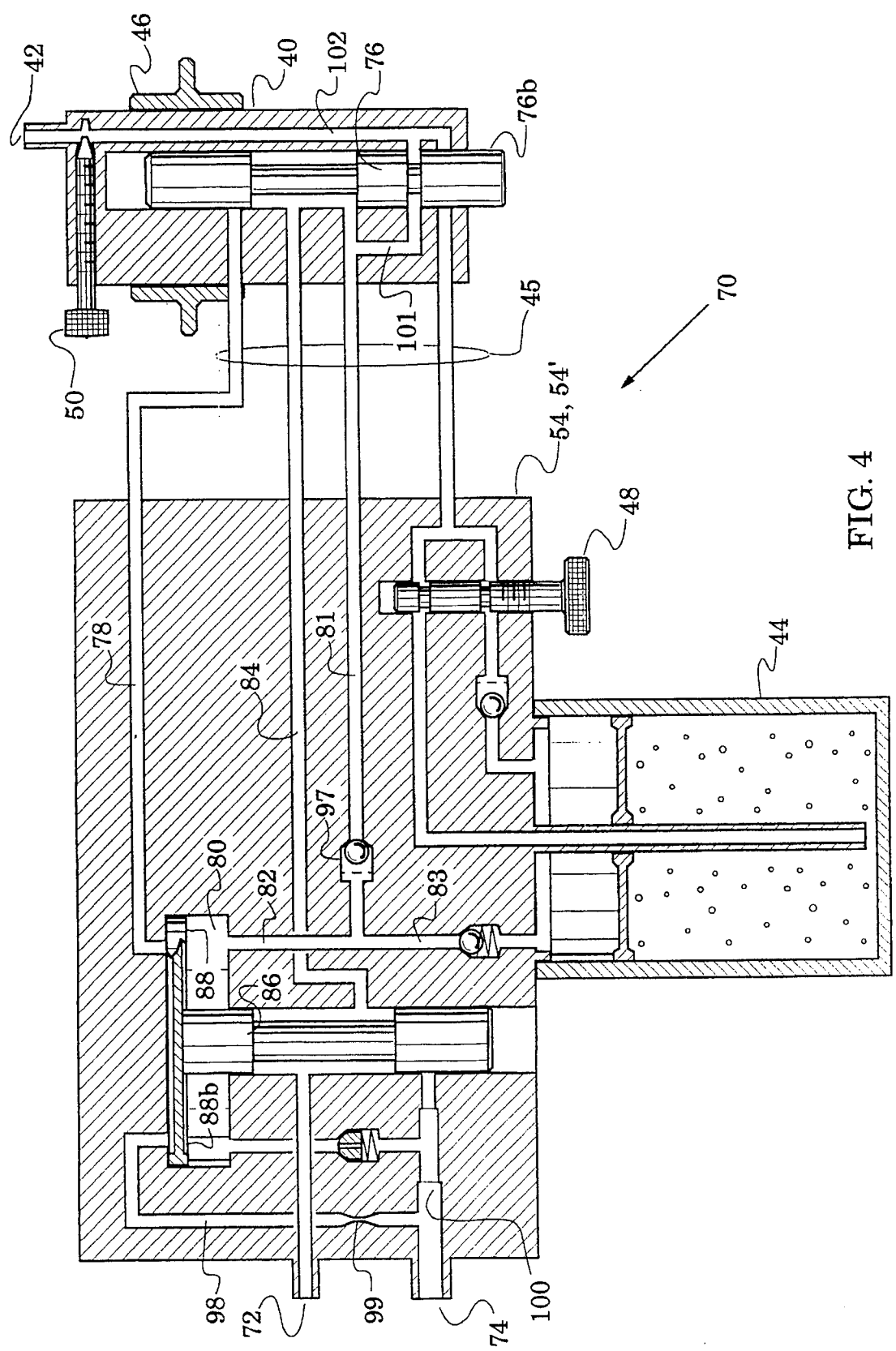
FIG. 4 a schematic illustrating another mode of the operational embodiment of FIG. 3.
Figure 5:
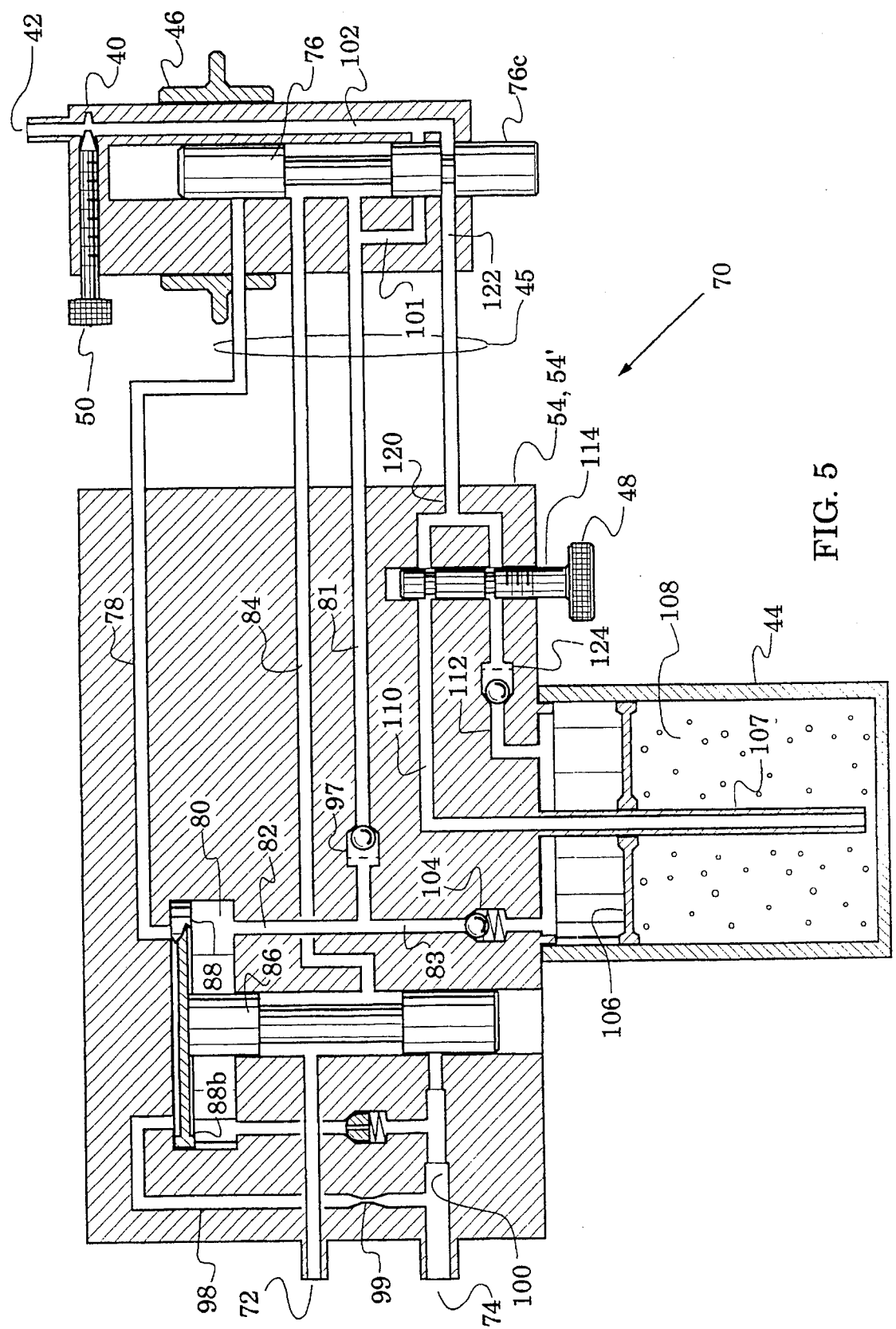
FIG. 5 is a schematic illustrating another mode of the operational embodiment of FIG. 3.

Attention is now directed to the details of FIG. 3 which is a schematic illustrating a preferred operational embodiment 70 of the embodiments 20, 30 of FIGS. 1, 2 and to FIGS. 4, 5 which illustrate other modes of the embodiment 70. In these figures, as described above, the syringe 40 extends from a hose 45 which is attached to a base 54 (and 54') having a mixture control knob 48 and a container 44 (and 44'). As shown, the hose 45 defines a plurality of flexible tubes to allow the syringe 40 to communicate with the base 54 (54'). The base 54 (54') defines a supply port 72 (the input port 56 of FIG. 1 and a port receiving one end of the double hose 64 of FIG. 2) and a tap port 74 (the output port 60 of FIG. 1 and a port receiving the other end of the double hose 64 of FIG. 2). As also described above, the syringe 40 defines an orifice 42 and has a sliding sleeve 46 and a flow control knob 50. In FIG. 3, the sleeve 46 is seen to be attached (e.g. by a pin 75) to a control valve in the form of a control spool valve 76 which is in a position 76a to supply water from a pressurized water supply attached to the water supply port 72 through a passage 84 and return passage 78 to a cylinder 80. This is the "off" mode referred to above. FIGS. 4, 5 illustrate respectively two other positions 76b, 76c defining two "on" modes in each of which, water from the supply port 72 is directed through passage 84 and passages 81, 82 to the other side of the cylinder 80 and through passages 81, 83 to the container 44 (44') (for clarity of illustration the sleeve 46 is shown only in section in FIGS. 4, 5).

In all three modes, the control spool valve 76 receives water from the supply port 72 through a passage 84 which communicates through a diverter spool valve 86 but it should be understood that in other embodiments of the invention the control spool valve 76 may communicate directly with the supply port 72.

In the "off" mode shown in FIG. 3, water supplied to the cylinder 80 causes a diverter piston 88, defined by the diverter spool valve 86, to go to the position 88a in which water is diverted to the tap port 74 for normal use of the water tap with which the apparatus is installed (e.g. the shower head 22 of FIG. 1, the sink tap 32 of FIG. 2). In this case, the syringe 40 would normally be placed in the holder 52 as shown in FIGS. 1, 2.

A passage 90 provides a path for water to be relieved from the back side of the piston 88 to the tap port 74. This passage 90 has a pressure control valve 92 with a restricted orifice therein. This orifice allows water flow but develops back pressure needed to move the piston 88 to the operational modes to be described in FIGS. 4, 5. The pressure control valve 92 also has spring release to protect the apparatus from damage in case of excessively high water pressure from the supply port 72. The tap port 74 defines a step 96 therein which lowers back pressure therein to enhance water flow through the passage 90. In the mode of FIG. 3, the water pressure delivered at the supply port 72 is available at the external tap connected to the tap port 74 and the external tap may be on or off as desired.

Attention is now directed to the two operational "on" modes depicted in FIGS. 4, 5. In both modes, spool valve positions 76b, 76c, shown in respectively FIGS. 4, 5, supply water through passage and passages 81, 82 to drive the diverter piston 88 from position 88a (FIG. 3) to position 88b. The diverter piston 88 is seen, therefor, to be reciprocable responsive to water supplied through passages 78, 82 connected to first and second control ports defined by the control spool valve 76. A one way valve 97 prevents reverse water flow through the control spool valve 76 as it transitions between positions 76b and 76a.

A passage 98 with a restriction 99 allows water from the upper side of the cylinder 80 to be relieved to the tap port 74. The restriction 99 develops back pressure to facilitate movement of the diverter piston 88 to the position 88a illustrated in FIG. 3. The tap port 7,1 defines a second step 100 to reduce back pressure therein and enhance flow through passage 98.

In the control spool valve position 76b of FIG. 4, water received from the supply port 72 is routed through passages. 101, 102 to exit from the orifice 42. In this operational mode water may be directed from the syringe 40 against teeth and gums and the flow rate of the water adjusted with a flow control valve in the form of a threaded needle valve (defined by the flow control knob 50) which can progressively restrict passage 102.

Finally, attention is directed to FIG. 5 illustrating the control spool valve position 76c. In this position, water received by the control spool valve 76 from the supply port 72 can no longer flow through passage 101 so that it is now directed through a spring urged pressure control valve 104 in passage 83 to urge a dispenser piston 106 to slide downward on a tube 107 into the container 44 (44') to exert pressure on a dental concentrate 108.

Water pressure via the passage 83 thus provides water via passage 112 and dental concentrate via the tube 107 and passage 110 to a mixer spools a needle valve 114. In the position shown in FIG. 5 the needle valve 114 allows substantially equal flows of water and concentrate into passage 120. It is apparent that movement of the threaded needle valve 114 by means of its knob 48 will increase the flow of one of these liquids through passage 120 at the expense of the other. The mixed fluids flow through the control spool valve 76 via passages 122,102 to issue from the orifice 42.

Thus, the container 44 (44') and its associated elements (e.g. piston 106, tube 107, passages 83, 110,112, needle valve 114) form a dispenser of a mixture of water and dental concentrate 108 through passage 120. A one way valve 124 in passage 112 inhibits contamination of water above the dispenser piston 106 with dental concentrate 108 during transitions between operational modes. The control spool valve 76 directs water to this dispensing means and also routes water to the orifice 42 when in position 76b (FIG. 4) and diluted dental concentrate to the orifice 42 when in position 76c (FIG. 5).

Although not explicitly shown in the apparatus 20 of FIG. 1 (or in FIGS. 3–5), the container 44 is removably attached to the base 54 by means well known in the art (e.g. threaded interface) so that it may be removed for refilling with dental concentrate 108.

In the apparatus 30 of FIG. 2, refilling is facilitated by a container removable lid 128. After the lid is removed the apparatus may be inverted to remove water in the container 44'. Because the dispenser piston 106 sealingly fits the container 44', the container inner wall is relieved proximate the lid 128 to facilitate water flow about the dispenser piston 106 when the apparatus is inverted to eliminate the water in the container 44'. After the apparatus 30 is placed back on the countertop 31, the piston 106 is pushed to the lower end of the container 44' and the container refilled with dental concentrate. A push rod may be provided with the apparatus 30 to facilitate returning the piston downward in the container 44'. Such a push rod could be removably mounted to the base 54' when not in use.

Figure 6:
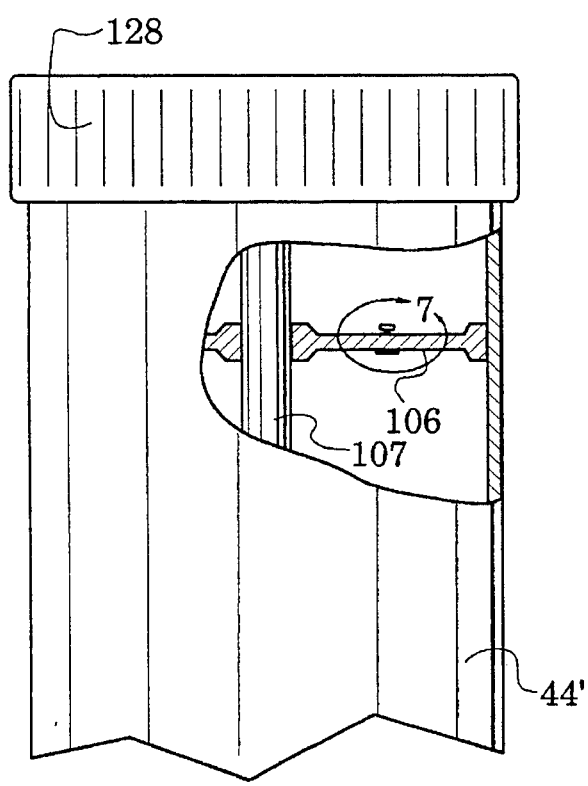
FIG. 6 is a partial elevation view of the container in FIG. 2.
Figure 7A:
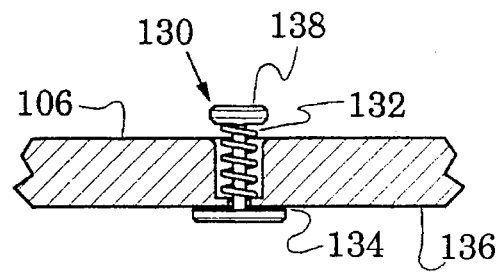
FIG. 7A is an enlarged view of the area within line 7 of FIG. 6.
Figure 7B:
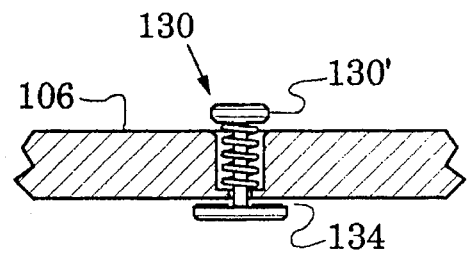
FIG. 7B is a view similar to FIG. 7A.

To facilitate pressing the piston 106 downward against air trapped behind it, a small relief valve 130 is disposed in the piston as shown in FIG. 6 which is a partial elevation view of the container 44' and in FIGS. 7A, 7B which are enlarged views of the area within the line 7 of FIG. 6. The relief valve 130 is normally urged by a spring 132 to compress a rubber seal 134 against the piston 106 lower surface 136. A knob 138 is defined at the end of the valve stem and manually pressing it downward places the valve 130 in position 130' illustrated in FIG. 7B. This allows air trapped below the piston 106 to be released as the piston 106 is depressed.

Another preferred operational embodiment 140, for the apparatus 30 of FIG. 2, is shown in FIG. 8 Which is an inverted, enlarged view similar to a portion of FIG. 3. The embodiment 140 enables the removal of water in the container 44' without inversion of the apparatus as described above. In this embodiment, a cap 141 is slidably-mounted to a lid 142 (e.g. by tongue and groove engagement therebetween) and the combination is mounted to a container 44' (e.g. by threaded engagement between lid 142 and container 44'). The cap 141 and lid 142 are urged apart by a spring 145. The cap 141 and lid 142 each have one way valves 146 comprising resilient washers 147 received over downward extending bosses 148 to respectively cover cap vents 150 and lid vents 152.

A rotary valve 160 is inserted into passage 83 to exhaust water trapped behind the piston 106 to the tap port 74. For normal operation, the valve 160 is turned to connect, with its bore 162, the pressure control valve 104 and the container 44'. In this position the bore 164 is oriented to face away from a passage 166 in the base 168 leading to the tap port 74. This position of the rotary valve 160 connects the pressure relief valve 104 to the container in a manner similar to that shown for embodiment 70 of FIGS. 3, 4 and 5.

To move the piston 106 downward in the, container 44', the rotary valve 160 is turned to the position illustrated in FIG. 8 which connects the container 44' via valve bores 162, 164 to the passage 166. The passage 166 is directed past the diverter valve 86 to tap port 74.

Depression of the cap 141 against the urging of the spring 145 causes air between the cap 141 and the lid 142 to be forced through the lid valves 146 as indicated by one lid washer 147 shown in broken line and arrows 170 (during this depression, the cap valves would be closed as shown by the solid line cap valve directly above the broken line open lid valve). When the cap is allowed to rise under urging of the spring 145', air is drawn in through cap valves 146 as indicated by one cap washer 147 shown in broken line and the arrows 172 (during this rise, the lid valves would be closed solid line lid valve directly below the broken line open cap valve). Repeated depression of the cap 141 thus increases the air pressure within the container 44' to depress the piston 106 as water trapped behind it exits, via the rotary valve 160 and passage 166, to the tap port 74.

The rotary valve 160 may define a manual adjustment member (e.g. a knob) that is accessible exterior to the base member 168 for adjustment of the valve position.

For clarity of illustration, other details necessary to the operational modes illustrated in FIGS. 3, 4 and 5 (e.g. 0 ring seals associated with diverter spool valve 86 and control spool valve 76) have not been shown where they are well known to one skilled in the art.

The teachings of the invention may be extended to an apparatus having an operational embodiment similar to the embodiment 70 illustrated in FIGS. 3–5 but without the diverter spool valve 86 and tap port 74. That is, an apparatus can be configured to operate from a pressurized liquid source without the need to selectively divert liquid to a water tap such as the showerhead 22 of FIG. 1 or sink tap of FIG. 2.

From the foregoing it should now be recognized that exemplary apparatus embodiments have been disclosed herein configured specifically for cleansing of teeth and gums. Generally, embodiments of the invention may be configured for generating a stream of water or cleansing solution for irrigating of any restricted access area. Although the described preferred embodiments have an orifice configured to define a fine stream of liquid it should be understood that the orifice may generally assume any shape. Apparatus in accordance with the present invention operate solely with water pressure and are, therefore, safe to use in any moist environment.

The preferred embodiments of the invention described herein are exemplary and numerous modifications, dimensional variations and rearrangements can be readily envisioned to achieve an equivalent result, all of which are intended to be embraced within the scope of the appended claims.

What is claimed is:

1. Apparatus operative from a pressurized first liquid supply, comprising:

dispension means, defining a container to hold a second liquid and an inlet and outlet communicative therewith, for dispensing a third liquid through said outlet when a first liquid is received at said inlet, said third liquid being a mix of said first liquid and said second liquid; and control valve means defining an orifice and receptive of the first liquid from said first liquid supply and the third liquid from said dispensing means outlet, for selectively directing said first liquid to said dispensing means inlet and for routing to said orifice a selected one of said first liquid and said third liquid, mixing means for adjustably mixing said first liquid and said second liquid to form said third liquid, said mixing means comprising a mixer spool valve.

2. Apparatus operative from a pressurized first liquid supply, comprising:

means, defining a container to hold a second liquid and an inlet and outlet communicative therewith, for dispensing a third liquid through said outlet when a first liquid is received at said inlet, said third liquid being a mix of said first liquid and said second liquid; and control valve means defining an orifice and receptive of the first liquid from said first liquid supply and the third liquid from said dispensing means outlet, for selectively directing said first liquid to said dispensing means outlet and for routing to said orifice a selected one of said first liquid and said third liquid, said control valve means further defining first and second control ports and comprising means for supplying said first liquid to a selectable one of said first and second control ports; and further comprising:

valve means, defining a tap port and responsive to the first liquid received from said first and second control ports, for selectively diverting the first liquid received from said first liquid supply to said tap port.

3. The apparatus of claim 2 wherein said diverting valve means comprises a diverter piston reciprocatively responsive to first liquid received from said first and second control ports.

4. The apparatus of claim 2 wherein said diverting valve means comprises a diverter spool valve.

5. Apparatus operative from a pressurized first liquid supply, comprising: means, defining a container to hold a second liquid and an inlet and outlet communicative therewith, for dispensing a third liquid through said outlet when a first liquid is received at said inlet, said third liquid being a mix of said first liquid and said second liquid; and control valve means defining an orifice and receptive of the first liquid from said first liquid supply and the third liquid from said dispensing means outlet, for selectively directing said first liquid to said dispensing means outlet and for routing to said orifice a selected one of said first liquid and said third liquid, said dispensing means comprising a dispenser piston slidably received in said container to be responsive to said first liquid directed there against, said apparatus further comprising means for moving said piston within said container to facilitate filling thereof with said second liquid.

6. Apparatus operative from a pressurized first liquid supply, comprising: a container for holding a second liquid;

a dispenser piston defining first and second sides and slidably disposed in said container to abut said second liquid with said second side;

a base member configured to carry said container, said base member defining a supply port connectable to said pressurized first liquid supply, a container inlet passage communicating with said dispenser piston first side and a container outlet passage communicating with said dispenser piston first and second sides;

a control valve defining a first liquid inlet, a first control port, a third liquid inlet and an orifice, said control valve configured to selectively connect said first liquid inlet to said first control port and to connect a selected one of said first liquid inlet and said third liquid inlet to said orifice; and means for connecting;
a) said base member supply port and said control valve first liquid inlet;
b) said control valve first control port and said container inlet passage; and
c) said container outlet passage and said control valve third liquid inlet.

7. The apparatus of claim 6 wherein:

said base member further defines a tap port; and said control valve further defines a second control port and is configured to connect a selected one of said first and second control ports to said control valve first liquid inlet;

and further comprising a diverter valve configured to connect said supply port to said tap port in response to first liquid received from said first and second control ports.

8. The apparatus of claim 6 further comprising: valve means for selectively communicating between said piston first side and said tap port; and means for increasing the pressure against said piston second side.

9. The apparatus of claim 6 wherein said container outlet passage comprises first and second mixer passages communicating respectively with said first and second dispenser piston sides;

and further comprising a mixer valve adjustably carried by said base member to selectively restrict said first and second mixer passages.

10. The apparatus of claim 6 further comprising a flow control valve for selectively restricting said orifice.

11. A method of forming an apparatus operative from a pressurized first liquid supply to dispense a liquid stream, comprising the steps of:

configuring a container to hold a second liquid;

disposing a dispenser piston having first and second sides slidably in said container to abut said second liquid with said second side;

forming a base member defining a first liquid inlet passage communicative with said dispenser piston first side and defining an outlet passage communicative with said dispenser piston first and second sides, said outlet passage thus mixing said first liquid and said second liquid to form a third liquid;

forming a control valve to define an orifice and receive first liquid from said first liquid supply and said third liquid from said outlet passage; and configuring said control valve to selectively direct said first liquid to said first liquid inlet passage and to route to said orifice a selected one of said first liquid and said third liquid.

12. The method of claim 11 further comprising the steps of: defining, with said control valve, first and second control ports;

configuring said control valve to selectively supply said first liquid to said and second control ports; and forming a diverter valve to define a tap port and to selectively divert first liquid received from said first liquid supply to said tap port in response to first liquid received from said first and second control ports.

13. A dental liquid mixing and dispensing apparatus powered and controlled by water pressure, said apparatus comprising:
 a) a stationary base for being connected to a pressurized source of water,
 b) a reservoir for holding a quantity of a second liquid,
 c) discharging means in communication with the reservoir for delivering a flow of said second liquid,
 d) an elongated flexible hose connected at one end to the base,
 e) a hand-holdable, light-weight portable control and dispensing unit connected to the other end of the hose, and having a manually operable flow control and a dispensing outlet,
 f) a separate mixing means disposed between the dispensing outlet on the one hand, and the second liquid discharging means and the water source on the other hand, said mixing means being selectively adjustable by the user to establish a user-set ratio of the flow of the pressurized water to the flow of the second liquid to the dispensing outlet, said mixing means being independent of the flow control of said hand-holdable unit and being operable to maintain said user-set ratio regardless of the mode of operation of the apparatus,
 said flow control on said hand-holdable unit being manually selectively operable to cause the apparatus to function in at least a selected one of the following two modes of operation to either 1) block all flow from said dispensing outlet, or 2) allow flow in said user-set ratio from said dispensing outlet.

14. The apparatus of claim 13 wherein said second mode of operation includes (i) providing a flow of the pressurized water from the source to the reservoir so as to actuate, by virtue of the pressure of the water, the discharge means to deliver a flow of the second liquid from said reservoir to the mixing means, (ii) providing a flow of the water from the source to the mixing means, (iii) passing said flows from (i) and (ii) through the user-set mixing means to provide a combined flow of the water and second liquid in the user-set ratio, and (iv) directing that combined flow to and out through the dispensing outlet.

15. The apparatus of claim 14 wherein said hose contains the following liquid carrying lines:
 a) a first line communicating with the source of the pressurized water for providing a flow of the water to the unit,
 b) a second line for providing a bypass for a return flow of the water from the unit,
 c) a third line for providing a return control flow of the water to the second liquid discharging means, and
 d) a fourth line communicating with the discharging means for receiving a flow of the second liquid mixed with the water to the unit.

16. The apparatus of claim 13 wherein said flow control is selectively operable to cause the apparatus to function in the following additional mode of operation to
 3) provide a flow of the water from the source on through the dispensing outlet.

17. The apparatus of claim 16 wherein said hand-holdable control and dispensing unit is proportioned and arranged to be held in one hand of a user, said unit having a single movable control member movable by a finger of that one hand while the hand holds the unit to selectively cause the apparatus to operate in any one of said three modes.

18. The apparatus of claim 17 wherein said hand-holdable unit contains a single shiftable spool valve movable between three operative positions that each cause one of said modes of operation.

19. A dental liquid mixing and dispensing apparatus powered and controlled by water pressure, said apparatus comprising:
 a) a stationary base for being connected to a pressurized source of a water,
 b) a reservoir for holding a quantity of a second liquid, said reservoir including discharging means for delivering a flow of said second liquid,
 c) an elongated flexible hose connected at one end to the base,
 d) a hand-holdable, light-weight portable control and dispensing unit connected to the other end of thee hose, and having a manually movable flow control and a dispensing outlet,
 e) a separate mixing means disposed between the dispensing outlet on the one hand, and the second liquid discharging means and the water source on the other hand, said mixing means being selectively adjustable by the user to establish a user-set ratio of the flow of the pressurized water to the flow of the second liquid to the dispensing outlet, said mixing means being independent of the flow control of said hand-holdable unit and being operable to maintain said user-set ratio regardless of the mode of operation of the apparatus,
 said flow control on said hand-holdable unit comprising a single movable control member, said control member being manually selectively movable to cause the apparatus to function in a selected one of at least the following three modes of operation to either:
  1) block all flow from said dispensing outlet, or
  2) provide a flow of the water from the source out through the dispensing outlet, or
  3) (i) provide a flow of the water from the source to the reservoir so as to actuate, by virtue of the pressure of the water the discharge means to deliver a flow of the second liquid from said reservoir to the mixing means, (ii) provide a flow of the first liquid from the source to the mixing means, (iii) pass said flows from (i) and (ii) through the user-set mixing means to provide a combined flow of the first and second liquids in the user-set ratio, and (iv) direct that combined flow to and out through the dispensing outlet.

20. The apparatus of claim 19 wherein said hand-holdable control and dispensing unit is proportioned and arranged to be held in one hand of a user, said movable control member being movable by a finger of that one hand while the hand holds the unit to selectively cause the apparatus to operate in any one of said three modes.

21. The apparatus of claim 20 wherein said hand holdable unit contains a single shiftable spool valve movable between three operative Positions that each cause one of said modes of operation.

22. The apparatus of claim 19 wherein said hose contains the following liquid carrying lines:
 a) a first line communicating with the source of the pressurized water for providing a flow of the water to the unit, b) a second line for providing a bypass for a return flow of the water from the unit, c) a third line for providing a return control flow of the water to the second liquid discharging means, and d) a fourth line communicating with the discharging means for receiving a flow of the second liquid mixed with the water to the unit.

23. A method of providing selected dental liquid flows of a main carrier liquid of pressurized water along and mixed with a supplemental liquid, said method comprising the steps of:

a) directing a flow of pressurizing water to a hand-holdable portable controller and dispenser unit having a dispensing outlet, b) providing a supply of a supplemental liquid at a stationary base location, c) setting a mixing means for a desired ratio of water flow to supplemental liquid flow, d) operating controls on the hand-holdable unit to select between the following three modes of operation:
1) discharging a flow of water from the dispensing outlet, or
2) blocking all flow from the dispensing outlet, or
3) (i) diverting at least a portion of the flow of water to the supply of supplemental liquid and utilizing the pressure of that flow of water to discharge a flow of the supplemental liquid from the supply, (ii) mixing a flow of main water with a flow of supplemental liquid in the desired ratio by directing said liquid flows through the set mixing means, and (iii) directing the mixed liquids to the dispensing outlet.

* * * * *

UNITED STATES PATENT AND TRADEMARK OFFICE
CERTIFICATE OF CORRECTION

PATENT NO. : 5,564,629
DATED      : October 15, 1996
INVENTOR(S) : William R. Weissman et al It is certified that error appears in the above-indentified patent and that said Letters Patent is hereby corrected as shown below:

Col. 1  line 49, after "Thompson" insert --5,220,914--.

Col. 1  line 56, after "mixing" delete --apparatus--.

Col. 2  line 36, after "Fig. 4" insert --is--.

Col. 3  line 16, after "orifice" delete --:--.

Col. 4, line 38, after "passage" insert --84--.

Col. 4, line 38, after "and" insert --return--.

Col. 4, line 50, change "7.1" to --74--.

Col. 5, line 5, change "spools a" to --spool or--.

Col. 5, line 57, change "Which" to --which--.

Col. 6, line 13, before "container" delete --,--.

Col. 6, line 25, change "145'" to --145--.

Col. 6, line 28, after "closed" insert --as shown by the--.

Col. 9, line 2, after "said" insert --first--.

UNITED STATES PATENT AND TRADEMARK OFFICE
CERTIFICATE OF CORRECTION

PATENT NO. : 5,564,629
DATED : October 15, 1996
INVENTOR(S) : William R. Weissman et al It is certified that error appears in the above-indentified patent and that said Letters Patent is hereby corrected as shown below:

Col. 10, line 59, change "hand holdable" to --hand-holdable--.

Signed and Sealed this

Eighteenth Day of February, 1997

Attest:

BRUCE LEHMAN

*Attesting Officer*  *Commissioner of Patents and Trademarks*